United States Patent [19]

Westland et al.

[11] Patent Number: 5,207,826
[45] Date of Patent: May 4, 1993

[54] BACTERIAL CELLULOSE BINDING AGENT

[75] Inventors: John A. Westland, Bothell; R. Scott Stephens, Auburn; William C. Johnston, Jr., Puyallup; Harold J. Rosenkrans, Seattle, all of Wash.

[73] Assignee: Weyerhaeuser Company, Tacoma, Wash.

[21] Appl. No.: 771,811

[22] Filed: Oct. 7, 1991

Related U.S. Application Data

[63] Continuation-in-part of Ser. No. 513,349, Apr. 20, 1990, abandoned.

[51] Int. Cl.$^5$ .............................................. C08L 1/02
[52] U.S. Cl. .................................. 106/163.1; 106/203; 106/204
[58] Field of Search ...................... 106/163.1, 203, 204

[56] References Cited

U.S. PATENT DOCUMENTS

| | | | |
|---|---|---|---|
| 4,183,997 | 1/1980 | Stofko .............................. | 106/163.1 |
| 4,374,702 | 2/1983 | Turbak et al. . | |
| 4,378,431 | 3/1983 | Brown, Jr. . | |
| 4,742,164 | 5/1988 | Iguchi et al. ...................... | 106/163.1 |
| 4,762,564 | 8/1988 | Bridgeford .......................... | 106/204 |
| 4,863,565 | 9/1989 | Johnson et al. ..................... | 162/150 |
| 4,929,550 | 5/1990 | Byrom . | |

FOREIGN PATENT DOCUMENTS

| | | |
|---|---|---|
| 0186495 | 7/1986 | European Pat. Off. . |
| 0206830 | 12/1986 | European Pat. Off. . |
| 0212289 | 3/1987 | European Pat. Off. . |
| 0228779 | 7/1987 | European Pat. Off. . |
| 0243151 | 10/1987 | European Pat. Off. . |
| 6111360 | 5/1986 | Japan . |
| 61-212295 | 9/1986 | Japan . |
| 61-215635 | 9/1986 | Japan . |
| 61-221201 | 10/1986 | Japan . |
| 8911783 | 12/1989 | PCT Int'l Appl. . |
| 8912107 | 12/1989 | PCT Int'l Appl. . |
| 1570487 | 7/1980 | United Kingdom . |

OTHER PUBLICATIONS

A. F. Turbak, et al., Microfibrillated Cellulose, A New Cellulose Product: Properties Uses and Commercial Potential, Journal of Applied Polymer Science Applied Polymer Symposium 37,815 (1983).

H. Yokota et al., Microfibrillated Substances and Their Application for Cellulose, Chitin and Chitosan, 1987 Inter. Dissolving Pulps Conference.

*Primary Examiner*—David Brunsman
*Attorney, Agent, or Firm*—Stoel Rives Boley Jones & Grey

[57] ABSTRACT

A binding agent comprising fiber strands of microbially produced cellulose is disclosed. The cellulose is synthesized by certain strains of microorganisms of the genus Acetobacter grown under agitated culture conditions to produce fine, interconnected fiber strands forming a three-dimensional reticulated structure. The binding agent is effective for binding fibers and fragments of material, such as natural and treated wood fragments and particles as well as synthetic materials, and it imparts wet and dry tensile strength to the bound material.

16 Claims, No Drawings

BACTERIAL CELLULOSE BINDING AGENT

This is a continuation-in-part of U.S. patent application Ser. No. 07/513,349, filed Apr. 20, 1990, now abandoned.

TECHNICAL FIELD

This invention relates generally to methods and agents for binding fibers and relatively large fragments and particles, and it relates more specifically to the use of microbially produced cellulose as a binding agent.

BACKGROUND OF THE INVENTION

Binding agents are typically mixed with fibers and pieces of material to hold the fibers together and to impart mechanical strength to the resultant fiber mixture. Conventional binding agents include various types of resins, glues and gums.

For many applications, it is desirable to use binding agents that strengthen the mixture without significantly changing its other properties, such as absorbency. Moreover, it is often desirable to employ binding agents that provide mechanical strength irrespective of whether the fiber mixture is in a wet or a dry state or changes between those two states.

Various types of polysaccharides have been used as thickeners, fillers, and the like for various applications. Microbially produced cellulose, including cellulose produced by competent strains of Acetobacter, has been adapted for use in a variety of applications.

Japanese Kokai Patent No. Sho 61(1986)-113601 discloses macerated cellulose substances and methods for manufacturing such substances. Cellulose produced by microorganisms, e.g. Acetobacter, having the structure of ribbon-format microfibrils entangled in a complex form, is macerated using mechanical shear force. Industrial applications for the macerated cellulose product include viscosifiers for cosmetic products or coating materials, strengthening food raw material bases, retaining water, improving food stability, as low calorie additives or emulsification stabilizing agents, as a reinforcer for polymers, especially aqueous-system polymers, and for use in a paper or solid form.

European Patent Application Publication No. 0 212 289 teaches absorbent, retentive cellulose pulp. Cellulose is microfibrillated, then frozen, subjected to solvent exchange, and treated with a crosslinking agent. The product exhibits increased absorption, fluid retention, and high wet resiliency, even after having been highly compressed. Applications include use in napkins, tampons, etc. to increase to total absorption capacity and wicking rate. European Patent Application Publication No. 0 209 884 is commonly assigned and also teaches freeze-dried, cross-linked microfibrillated cellulose for use in absorbent products.

U.S. Pat. No. 4,374,702 teaches microfibrillated celluloses (MFC) having properties different from previously known celluloses, but not substantially chemically changed from the cellulose starting material. The U.S. Pat. No. '702 patent teaches that MFC is suitable for use with paper products and non-woven sheets made, for example, using Rayon, to improve their strength. The results are said to establish that MFC is valuable as a binder for paper and other materials having non-woven constructions.

Japanese Kokai Patent No. Sho 61(1986)-221201 teaches a method of manufacturing fine cellulose crystals wherein microbially produced cellulose is suspended in one or more media selected form an acid stronger than 1N, a base stronger than 1N, a polar solvent and an ammoniacal solution of a metal oxide, and mechanically ground before or after drying. The cellulose substance is in the form of tangled ribbon-shaped microfibrils and is in a gel state. Fine cellulose crystals obtained using this method are about 0.01 to $0.1\mu$ in size. They are used in food additives, as agents in drugs, cosmetics and paint, in additives, in binders, in high strength composite materials, and as a support material for chromatography. Japanese Kokai Patent No. Sho 61(1986)-215635 teaches fine cellulose crystals prepared in accordance with the methods disclosed in the previous reference. The fine cellulose powder may be used as a bonding agent by applying a suspension of it between boards.

European Patent Application No. 0 243 151 teaches a microbially-produced cellulose gel modified by physical or chemical bonding with an animal cell adhesive protein, and/or by substituting the hydrogen of at least some hydroxyl groups with a positively or negatively charged organic group. The gel is useful as a carrier for mass culture of animal cells or as a medical vulnerary cover (i.e. artificial skin). The gel may be dried and returned to a gel state. Included as auxiliary materials to be complexed are non-woven fabrics and other fabrics composed of natural fibers or man-made fibers, films, paper sheets and porous films, organic or inorganic granules of alumina, glass and crystalline celluloses, and other materials. The system to be complexed may be incorporated in the culture media and the cellulose formed directly on or in the substance, or the gel may be impregnated or backed with the substance to be complexed, or the gel may be disintegrated and then complexed with the substance.

Japanese Kokai Patent No. Sho 61(1986)-212295 teaches methods of manufacturing bacterial cellulose in cultures of inositol or phytic acid. The cellulosic materials are edible and having application in the food industries, in maintaining the viscosity of food, cosmetics, and paints, and for food-base reinforcements, water retention, stability enhancement, low calorie additives, and emulsion-stabilization aids. Degradation products of cellulosic materials having microfibrillar structures are used for paper-like or solid products and in various industrial materials because of their high tensile modulus.

PCT Publication No. WO 89/11783 teaches applications for microbial cellulose including in situ application to restore and protect paper documents, especially fragile, acid-damaged documents, microchips, electronic components, circuit boards, and archeological artifacts. Use of microbial cellulose in the manufacture of latex items, such as condoms, and in the preparation of currency and other types of paper is also disclosed.

PCT Publication No. WO 89/12107 teaches specialty products utilizing microbial cellulose, including: nonwovens and films, specialty papers, filtration and separation media such as membranes; specialty carriers for battery fluid and fuel cells; coating metals on bacterial cellulose to produce materials having special electronic properties; carriers for foods, cosmetics, skin/hair treating materials and internal drugs; mixing agents and viscosity modifiers for surface coatings, paints, fillers, plasters, glues, adhesives, grouts and caulks; specialty fillers such as carbonized fillers for use as polymer fillers; light transmitting optical fibers; wavelength and other electromagnetic and radiation modifying materials; microfiller blends, especially with melt-blown and other polyolefin fillers; substrate, e.g. culture media; foods, food substrates and fiber substitutes; specialty laboratory uses; specialty lint-free clothing; synthetic leather and other textured and special appearance surfaces; diet fiber substitutes; blends with other fibers such as cotton, polyesters and nylons in woven and non-woven fabrics; and moisture-absorbing, soil-enhancing additives and conditioners. Bacterial cellulose was also used to promote seedling and spore germination. This publication teaches that microbial cellulose pellicles and other variants are useful as gums and gels for a wide variety of applications.

A. F. Turbak, et al., in "Microfibrillated Cellulose, A New Cellulose Product: Properties, Uses and Commercial Potential", Journal of Applied Polymer Science: Applied Polymer Symposium 37:815 (1983), teach preparation of microfibrillated cellulose (MFC) and applications for MFC as thickeners to yield viscous mixtures that exhibit thixotropic properties and suspend solid particles. Applications include: food products; cosmetics; paints; paper and non-woven textiles; oil field services; and medical carriers and barriers.

H. Yokota, et al., in "Microfibrillated Substances and Their application for Cellulose, Chitin and Chitosan, "1987 International Dissolving Pulps Conference/TAPP1 Proceedings, teaches preparation of microfibrillated substances, and viscosity and water retention values for the prepared product. Applications include binders for high performance paper, including inorganic papers and dietary fibers.

As is illustrated by the references described above, it is known to use various types of cellulose, including microbially produced cellulose, in a variety of applications. Cellulosic material is typically used to bind or strengthen woven or non-woven fibrous materials, fine particulate materials, or to confer enhanced rheological properties to various suspensions. To the inventors' knowledge, microbially produced cellulose has not been used in applications involving larger fragments of material, such as biomass fragments, relatively large particulate materials, or the like.

Hydraulic mulches comprise relatively large fragments of particles of material, such as biomass fragments, that are mixed with water to form a slurry. Binding agents are typically added to hydraulic mulch slurries to provide enhanced structural integrity upon application of the mulch. The slurry is sprayed onto the ground, effectively inhibiting soil erosion. Seeds may additionally be incorporated in the slurry, in which case the mulch protects the seeds and soil from adverse weather conditions and retains moisture to promote germination. Fertilizers and other plant growth and soil stabilization aids may also be included in hydraulic mulches.

Binding agents employed in mulches are commonly referred to as "tackifiers", with the hydraulic mulch product containing tackifier being referred to herein as the tackified hydraulic mulch. Guar gum is conventionally used as a tackifier, but it has a number of disadvantages. For instance, guar gum, which is generally used in the form of a finely ground powder, is difficult to disperse through a hydraulic mulch slurry to produce a uniformly tackified hydraulic mulch. In this regard, conventional hydraulic mulching equipment lacks the power necessary for generating the significant shear forces required to provide adequate premixing of the gum and hydraulic mulch. The tackifier/binding agent component of the tackified hydraulic mulch enhances the strength and integrity of a mat-like tackified mulch structure and may assist in adhering the mat-like mulch structure to the surface upon which it is applied. Consequently, non-uniformly tackified hydraulic mulches may exhibit reduced structural integrity and reduced adherent ability, which may result in partial removal of the mulch components from the surface upon which they are applied by wind, rain, etc.

Binding agents that maintain the strength and integrity of the mixture despite changes in the moisture content of the material are desirable in many applications, including the tackified hydraulic mulch application described above. Other such applications include numerous paper products, such as paper towels, wipes, tissues, or the like, which generally comprise natural or treated fibrous material. These products (hereafter collectively referred to as "fibrous products") may comprise natural wood pulp fibers, or wood pulp fibers which have been chemically and/or physically treated to impart desired properties. For example, wood pulp fibers may be treated to increase the absorbency of the product. It can be appreciated that binding agents used in the manufacture of fibrous products will be especially advantageous if they provide strength despite changes in the moisture content of the fibrous product.

SUMMARY OF THE INVENTION

The present invention is directed to an agent for binding relatively large fragments and particles, such as biomass fragments, comprising bacterial cellulose synthesized by certain microbial strains of the genus Acetobacter. The microorganisms are cultured under agitated cell culture conditions to produce very fine interconnected cellulosic fiber strands forming a highly reticulated three-dimensional structure.

It is believed that the bacterial cellulose binding agent of the present invention operates primarily by the mechanism of physical entanglement to bind together relatively small fibers of material. Different mechanisms are operative in the binding of relatively large fragments and particles. Examination of fragments bound with the bacterial cellulose binding agent of the present invention reveals that the highly reticulated cellulose fibers are distributed over and adhere to the surface of substrate fragments. There does not appear to be a substantial degree of penetration by cellulose fibers into the structure of the substrate fragments. The binding agent may be used to bind a wide variety of natural and synthetic materials, such as natural wood fibers, fiber bundles and fragments; chemically or physically treated wood fibers, fiber bundles and fragments; natural or treated plant-derived fibers, fiber bundles and fragments such as bagasse, hemp, flax, wheat, straw and other natural substances; and synthetic fibers and fragments, such as Kevlar ®, rayon and polypropylene, as well as other materials having similar physical properties.

The binding agent of the present invention effectively binds fibers of various sizes, ranging from microscopic fibers (for example, cellular wood fibers) to fibers several centimeters in size (for example, multicellular wood fragments). Microbial cellulose produced according to the methods described herein is especially suitable for binding relatively large fragments and particles of material, such as biomass materials, having average particle lengths (length being defined as the dimension having the greatest magnitude) on the order of at least about 0.3 to about 2.0 inches and average particle diameters of at least about 0.02 to about 0.2 inches. Although cellulosic materials have been used to assist in binding very small diameter fibers and fine particulate materials by means of physical entanglement, it is unexpected that microbial cellulose could effectively bind fragments having particle lengths and diameters many orders of magnitude greater than the corresponding dimensions of the microbial cellulose. In general, binding of increasingly larger fragments is accomplished using larger quantities of bacterial cellulose binding agent.

In one embodiment of the present invention, bacterial cellulose is used as a tackifier for hydraulic mulches. The binding agent of the present invention has been found to be an effective tackifier that enhances the performance of hydraulic mulches as compared to heretofore available tackifiers, such as guar gum. The physical properties of bacterial cellulose produced according to methods described herein and physical entanglement of bacterial cellulose with mulch fragments enhances the integrity and strength of the tackified mulch structure, and provides enhanced fragment-to-fragment bonding. The bacterial cellulose binding agent of the present invention imparts significant structural integrity to the mat-like mulch structure formed after spraying, as demonstrated by increased wet and dry tensile indices. Moreover, the binding agent is readily dispersed within the mulch slurry, thereby eliminating the need for longer slurry mixing times to insure adequate hydration of the tackifier. Unlike conventional gum tackifiers, the bacterial cellulose binding agent does not form a crust after the tackified mulch slurry dries.

In another embodiment of the present invention, the bacterial cellulose binding agent is employed to bind fibrous products to increase the wet and dry tensile strength of the products. The natural hydrophilicity of the microbially produced cellulose binding agent futhermore enhances the absorbency of the fibrous product in which it is used.

DESCRIPTION OF PREFERRED EMBODIMENTS

Bacterial Cellulose Binding Agent

Certain strains of microorganisms of the genus Acetobacter produce large quantities of cellulose when they are grown under agitated culture conditions. Acetobacter is characteristically a gram-negative, rod-shaped aerobic bacterium. Its metabolism is respiratory rather than fermentative. It is further distinguished by the ability to produce multiple poly $\beta$-1,4-glucan chains of cellulose under agitated culture. Multiple cellulose chains or fiber strands are synthesized at the bacterial surface at sites external to the cell membrane. The cellulose fiber strands produced by these microorganisms, although chemically similar to cellulose produced from wood pulp, differ in a number of important respects. An important difference is that cellulose fiber strands produced by Acetobacter are about two orders of magnitude narrower, having diameters of about 0.10 to 0.20 microns, than typical wood pulp cellulose fibers. Characteristics of cellulose-producing bacteria and preferred growth and agitated culture conditions are fully described in U.S. Pat. No. 4,863,565, entitled "Sheeted Products Formed From Reticulated Microbial Cellulose," which is herein incorporated by reference in its entirety.

Preferred embodiments of the bacterial cellulose binding agent of the present invention are produced under agitated culture conditions by any species or variety of bacterium within the genus Acetobacter that produces cellulose under agitated cell culture conditions. Such species have been classified both as *Acetobacter aceti* subsp. *xylinum* and as *Acetobacter pasteurianus*. The bacterial cellulose used in the following specific examples was produced from a strain of *Acetobacter aceti* var. *xylinum* having properties similar to or grown as a subculture of ATCC Accession No. 53263, deposited Sep. 13, 1985, or Accession No. 53524, deposited Jul. 25, 1986, under the terms of the Budapest Treaty. The bacteria may be cultured under conditions similar to those described below.

The base medium preferred for use with cellulose-producing microbial cultures is referred to as CSL medium. A suitable CSL medium comprises:

| Ingredient | Final Conc. (mM) |
| --- | --- |
| $(NH_4)_2SO_4$ | 25 |
| $KH_2PO_4$ | 7.3 |
| $MgSO_4$ | 1.0 |
| $FeSO_4$ | 0.013 |
| $CaCl_2$ | 0.10 |
| $Na_2MoO_4$ | 0.001 |
| $ZnSO_4$ | 0.006 |
| $MnSO_4$ | 0.006 |
| $CuSO_4$ | 0.0002 |
| Vitamin mix | 10 mL/L |
| Carbon source | As later specified |
| Corn steep liquor | As later specified |
| Anti-foaming agent | 0.01% v/v |

A suitable vitamin mix may be formulated as follows:

| Ingredient | Conc. (Mg/L) |
| --- | --- |
| Inositol | 200 |
| Niacin | 40 |
| Pyridoxine HCl | 40 |
| Thiamine HCl | 40 |
| Ca Pantothenate | 20 |
| Riboflavin | 20 |
| p-Aminobenzoic acid | 20 |
| Folic acid | 0.2 |
| Biotin | 0.2 |

The carbon source generally comprises monosaccharides or mixtures thereof, such as glucose and fructose, disaccharides such as sucrose, and mixtures of mono- and disaccharides. The carbon source may also be supplied as a complex mixture of sugars, such as molasses or plant biomass hydrolysates such as wood hydrolysate, straw, sorghum, and the like. Other carbohydrate derivatives, such as mannitol and sorbitol may also serve as carbon sources in culture media. The carbon source is typically provided in concentrations of about 0.5% to about 7.0% (w/v). The final pH of the medium is about 5.0, ±0.2.

Corn steep liquor, yeast extract, casein hydrolysate, ammonium salts or other nitrogen-rich substances may be sued as a general source of nitrogen, amino acids, minerals and vitamins. Corn steep liquor is preferred, and suitable concentrations thereof range from about 0.1% to about 10% (v/v). Cell culture media comprising about 5% (v/v) corn steep liquor is preferred for shaking flask cultures. In fermentors, an initial concentration of about 2% (v/v). corn steep liquor is supplemented during the fermentation run with additional aliquots of corn steep liquor. Corn steep liquor varies in composition, depending upon the supplier and mode of treatment. A product obtained as Lot E804 from Corn Products Unit, CPC North America, Stockton, Calif., may be considered typical and has the following composition:

| Major Component | % |
| --- | --- |
| Solids | 43.8 |
| Crude protein | 18.4 |
| Fat | 0.5 |
| Crude fiber | 0.1 |
| Ash | 6.9 |
| Calcium | 0.02 |
| Phosphorous | 1.3 |
| Nitrogen-free extract | 17.8 |
| Non-protein nitrogen | 1.4 |
| NaCl | 0.5 |
| Potassium | 1.8 |
| Reducing sugars (e.g. dextrose) | 2.9 |
| Starch | 1.6 |

Bacteria were first multiplied as a pre-seed culture using CSL medium with 4% (w/v) glucose as the carbon source and 5% (w/v) corn steep liquor. Cultures were grown in 100 mL of the medium in a 750 mL Falcon #3028 tissue culture flask at 30° C. for 48 hours. The entire contents of the culture flask were blended and used to make a 5% (v/v) inoculum of the seed culture. Pre-seeds were streaked on culture plates to monitor for homogeneity and contamination. Seed cultures were grown in 400 mL of the above-described culture medium in 2 L baffled flasks in a reciprocal shaker at 125 rpm at 30° C. for two days. Seed cultures were blended and streaked to monitor for contamination before further use.

Bacterial cellulose was formed in a continuously stirred 14 L Chemap (or larger) fermentor at 30° C. and ambient pressure using an initial 12 L culture volume inoculated with 5% (v/v) of the seed cultures. An initial glucose concentration of 32 g/L in the medium was supplemented during the 72-hour fermentor run with an additional 143 g/L added intermittently during the run. In similar fashion, an initial 2% (v/v) corn steep liquor concentration was augmented by the addition of an amount equivalent to 2% by volume of the initial volume at 32 hours and 59 hours. Cellulose concentration reached about 12.7 g/L during the fermentation. Throughout the fermentation, dissolved oxygen concentration was maintained at about 30% air saturation.

Following fermentation, cellulose was dewatered. The remaining cellulose was extracted with a basic solution at a pH of approximately 13 or higher at 60° C. for 2 hours. After extraction, the cellulose was washed with deionized water to remove residual alkali and bacterial cells. The purified microbially produced cellulose was maintained in wet condition for further use. It will be clear to one of ordinary skill in the art that various modifications may be made to the above-described methods of producing bacterial cellulose. The bacterial cellulose produced under stirred or agitated culture conditions. The bacterial cellulose produced under stirred or agitated culture conditions as described above, (hereafter referred to as "BAC") has a microstructure quite different from that produced by bacteria grown in conventional static cultures. BAC is a reticulated product forming a substantially continuous, three-dimensional network of branching interconnected fiber strands. The average cross-sectional area of BAC fiber strands is considerably less than the average cross-sectional area of cellulose fiber strands produced by conventional wood pulping techniques. In this regard, the average diameter of BAC fiber strands is approximately 0.10–0.20microns, while softwood pulp fiber strands average about 30 microns in diameter. Microbially produced cellulose having these physical characteristics is suitable for use as a binding agent according to the present invention.

The relatively small diameters of the BAC fiber strands, and the continuous, reticulated network of BAC provide an agent that binds fibers of material by physical entanglement with those fibers. Moreover, BAC effectively binds relatively large fragments and particles of material. The inventors postulate that large fragments of materials such as biomass are bound as a consequence of distribution of the highly reticulated BAC fibers over the surface area of two or more fragments and adherence of the BAC fibers to the fragments. This phenomenon produces enhanced fiber-to-fiber bonding that results in materials having enhanced structural integrity. The small-diameter BAC fiber strands provide a large surface area per unit volume of BAC. This large surface area of the binding agent, in conjunction with the natural hydrophilicity of the bacterial cellulose, greatly enhances the absorbency of the bound product. The resultant mass of bound material ("bound product") exhibits substantial mechanical integrity under wet and dry conditions, as demonstrated by wet and dry tensile index measurements.

BAC may be used as a binding agent with any of a variety of fibers fragments, including: natural wood fibers and fragments; chemically or physically treated wood fibers and fragments; plant-derived fibers and fragments, such as bagasse, hemp, flax, wheat, straw and other natural substances; chemically or physically treated plant-derived fibers and fragments; and synthetic fibers and fragments, such as Kevlar®, rayon, polypropylene and the like. BAC may also be mixed with an inert extender which is chemically non-reactive with BAC to provide an extending binding agent.

BAC is especially effective as a binding agent for relatively large fragments and particles having average particle lengths on the order of at least about 0.3 to about 2.0 inches and average particle diameters of at least about 0.02 to about 0.2 inches. Although the reticulated BAC fiber strands are orders of magnitude smaller than the substrate particles, BAC is an effective binding agent for such materials, and is especially suitable for use as a binder for biomass fragments in applications such as hydraulic mulches.

The BAC binding agent of the present invention is generally mixed with fibers and/or fragments to be bound to form a mixture comprising from about 0.2% to about 20% BAC, and more preferably from about 0.5% to about 10% BAC, on a dry weight basis. An aqueous liquid is preferably added to the fiber mixture to achieve a solids content of about .1% to about 50% on a dry weight basis, and more preferably about 2% to about 10%. The fiber mixture is thereafter processed as necessary to achieve properties of the desired final product.

EXAMPLE I

Hydraulic Mulch Having Bacterial Cellulose Binding Agent

According to one preferred embodiment of the present invention, BAC binding agent is used as a tackifier for hydraulic mulches. Mulches comprising wood fragments as manufactured by Weyerhaeuser Company of Tacoma, Wash., under the trademark Silva-Fiber®, are suitable. Representative ranges of fragment length distributions for Silva-Fiber® mulches are as follows:

| Fragment Length (inches) | Alder | Hemlock | Aspen |
|---|---|---|---|
| >2.00 | 5.1% | 17.4% | 2.1% |
| 1.125-2.00 | 4.4% | 4.5% | 2.0% |
| .875-1.125 | 15.9% | 11.8% | 16.6% |
| .625-.875 | 26.1% | 30.2% | 29.2% |
| .375-.625 | 33.8% | 26.0% | 30.9% |
| .187-.375 | 10.5% | 8.3% | 11.2% |
| <0.187 | 1.7% | 1.0% | 2.0% |

The range of fragment diameter distributions for Silva-Fiber® mulches is generally from about 0.08 to about 0.2 inches. Average fragment diameters are generally between about 0.02 and about 0.2 inches.

Virgin red alder fragments having a fragment length distribution similar to that shown for alder, above, and an average fragment diameter distribution were used for experimental purposes. Several tackified hydraulic mulch slurries using various amounts of BAC and conventional guar gum tackifiers were produced to compare the efficacy of the tackifier compositions. The tackified hydraulic mulch slurries were processed into discrete pads and tested to assess wet and dry tensile strength according to the test procedures described below.

Tackified hydraulic mulches having the following tackifier concentrations on a dry weight basis were prepared: 0% tackifier; 1.5% BAC tackifier; 1.5% guar tackifier; 3.0% BAC tackifier; 10% BAC tackifier; and 1.5% BAC+1.5% guar tackifier. For each hydraulic mulch composition, 15 grams of red alder wood fragments (dry weight basis) were weighed to the nearest 0.1 gram and placed into a stainless steel blending cup (Hamilton Beach #M-110E). The selected amount of tackifier was weighed to the nearest 0.01 gram, added to the hydraulic mulch in the blending cup, and 750 mL of deionized water were added to the blending cup. The mulch slurry was prepared in a Hamilton Beach blender (model #936-2) that was set to medium speed for seven minutes. The agitator on the mixing shaft was a low shear, one piece button type (Hamilton Beach #3036-940-0000).

A British Standard hand sheet mold as employed in the pulp and paper industry was used to form the tackified hydraulic mulch slurry into a pad. To this end, the cylinder was closed and partly filled with 750 mL of water. The slurry was poured into the cylinder, and the diluted slurry was agitated for ten seconds by bubbling air from beneath the screen.

The cylinder was drained through the screen and then opened. A wet blotter paper was placed over the pad and the cylinder was closed. A vacuum of 500 mm Hg was applied from below the screen for ten seconds to remove the excess water and to consolidate the pad. The cylinder was then opened and the blotter was removed from the pad.

The pad was removed from the cylinder by a small blast of compressed air supplied from below the screen. The pads were placed on a non-stick sheet and dried in a convection oven for 16 hours at 85° C. Dried test pads were cut to 5 cm by 10 cm with a knife-edge die and a hand press. Ten pads were made for each selected tackified hydraulic mulch composition. Pad thicknesses and weight were measured and average basis weight (g/m²) and density (g/cm³) were calculated.

A test jig having a pair of bar clamps was attached to a Constant Strain Rate machine (Instron 1122). Each clamp extended completely across one end of the test pad and was clamped to that end to apply approximately 5 to 25 psi (pressure) on the pad. Each 1' clamp (jaw width) covered approximately 25% of the total surface area of the pad. The clamps (hence, the pad ends) were pulled apart at a strain rate of 2.54 cm per minute, and the force required to break the sample was measured. Tensile strength of the pads was quantified as a tensile index (Nm/g), which was computed as the breaking load per basis weight.

Test indices were computed for test pads having tackified hydraulic mulches with various tackifier compositions in a dry state and in a wet state. A separate set of control pads (i.e., pads having no added tackifier) was also tested in wet and dry states. Test pads tested in the wet state were soaked in deionized water for 30 minutes prior to testing. All test pads were conditioned to 21° C. and 50% relative humidity for 24 hours prior to testing. Test results are shown in Table I.

TABLE I

| TACKIFIER DRY WT. (%) | | AVE. PAD BASIS WT. | AVE. PAD DENSITY | TENSILE INDEX DRY | INDEX WET |
|---|---|---|---|---|---|
| BAC | GUAR | (g/m²) | (g/cm³) | (Nm/g) | (Nm/g) |
| 0 | 0 | 657 | 0.09 | 0.13 | 0.01 |
| 0 | 1.5 | 685 | 1.10 | 0.28 | 0.02 |
| 1.5 | 0 | 726 | 0.11 | 1.38 | 0.05 |
| 1.5 | 1.5 | 713 | 0.11 | 1.34 | 0.11 |
| 0 | 3.0 | 719 | 0.09 | 0.41 | 0.05 |
| 3.0 | 0 | 749 | 0.13 | 3.07 | 0.13 |
| 10 | 0 | 775 | 0.17 | 8.62 | 0.33 |

It is evident from the averaged results shown in Table I that the BAC tackifier of the present invention provides tackified hydraulic mulches having greater wet and dry tensile strength (i.e., a higher tensile index) than is provided by an equivalent amount of guar gum tackifier. In this regard, the tensile index (dry) for a test pad having 1.5% BAC tackifier is about 3.5 times greater than the tensile index of a test pad having 1.5 % guar. Results for test pads containing BAC demonstrate that over the range of BAC tackifier amounts tested, the wet and dry strength of the tackified mulch increased nearly linearly with increasing amounts of BAC tackifier. In addition, the results for the test pad with a combination of BAC and guar gum tackifier indicates an enhanced wet tensile strength compared to guar or BAC tackifier alone, and a dry tensile strength equivalent to BAC and superior to guar alone.

EXAMPLE II

Tackified Hydraulic Mulches Prepared With Extended Tackifiers

BAC may be extended or premixed with other materials in order to provide the tackifier in a form with lower moisture content and improved handling characteristics. It was found that such "extended" tackifiers provide tackified hydraulic mulches having enhanced tensile strength. The extended tackifiers were prepared by blending BAC with Silva-Fiber® or clay (Ansilex) to give extended tackifiers having the following compositions: 90% Silva-Fiber®/10% BAC, 80% Silva-Fiber®/20% BAC, and 70% clay/30% BAC. It is contemplated that other extenders, such as guar gum, plantago, alginates, and other mucilages, carboxymethyl cellulose, peat, saw dust, synthetic polymeric materials, and the like may be mixed with BAC to form a suitable extended tackifier. Blending was accomplished in a Hobart mixer. The Silva-Fiber®/BAC extended tackifier was used as prepared. The clay/BAC extended tackifier was pressed to remove water and allowed to air-dry overnight. The air-dried material was ground in a Wiley mill fitted with a 1 mm screen. The moisture content of the extended tackifier was also varied to determine the effect thereof. The moisture content of the extended tackifiers was measured with a Cenco moisture balance (Model #26675).

Each extended tackifier was incorporated into hydraulic mulches to be tackified at several concentration levels to achieve tackified hydraulic mulches having BAC concentrations in the final tackified mulch composition of from 0.5% to 2.0% (weight percent on a dry weight basis). Control test pads having no tackifier were also formed and tested.

The results presented in Table II indicate that each extended tackifier composition enhanced the tensile strength of the tackified hydraulic mulch, compared to mulch having no tackifier (Test Sample 1). Moreover, a comparison of the results of test pad samples 2-5 with samples 6-9 suggests that the extender mulch/BAC tackifiers provide greater tensile strength to the tackified mulch composition as the moisture content of the tackifier (i.e., prior to mixing with the hydraulic mulch to be tackified) is increased from 30% to 45%. The use of clay in the extend tackifier composition may provide relatively high wet and dry strengths using lower moisture contents.

in a 3% (dry weight basis) slurry of BAC at a ratio of 70% urea to 30% BAC (w/w ratio). This mixture was then dried and repowdered.

One hydraulic mulch slurry prepared and tested contained no tackifier. The tackified hydraulic mulch prepared and tested contained the BAC/urea combination described above, having 1.5% BAC tackifier by weight in the tackified hydraulic mulch. Test pads were prepared and tested in accordance with the procedures set forth above to compare the wet and dry tensile indices thereof, and the results of that testing are set forth in Table III.

TABLE III

| TACKIFIER CONTENT | BASIS WEIGHT g/m² | TENSILE INDEX | |
|---|---|---|---|
| | | DRY (Nm/g) | WET (Nm/g) |
| No | 657 | 0.13 | 0.01 |
| Yes | 772 | 0.80 | 0.06 |

The BAC/urea tackifier containing test pad exhibited essentially the same wet strength as tackified test pads containing BAC alone (See Table I), and improved wet and dry tensile strength compared to the control sample which was not tackified.

EXAMPLE IV

Hydraulic Mulch Having Bacterial Cellulose Binding Agent

According to embodiments of the present invention illustrated in Examples I–III, the tackifier is added to a previously prepared mulch slurry to provide a tackified hydraulic mulch. In an alternative embodiment of the present invention, the tackifier may be added to the mulch at an earlier stage, such as during mulch prepara-

TABLE II

| Test Samp. No. | Extended Tackifier Composition (%, Dry Basis) | Ext. Tackifier Moisture Content (%, Dry Basis) | BAC Conc. (% Dry Basis) | Tensile Index | |
|---|---|---|---|---|---|
| | | | | Dry (Nm/g) | Wet (Nm/g) |
| 1 | 0% | — | 0% | 0.18 | 0.017 |
| 2 | 90% Mulch/10% BAC | 30% | 0.5% | 0.28 | 0.027 |
| 3 | 90% Mulch/10% BAC | 30% | 1.0% | 0.53 | 0.025 |
| 4 | 90% Mulch/10% BAC | 30% | 1.5% | 0.78 | 0.046 |
| 5 | 90% Mulch/10% BAC | 30% | 2.0% | 0.66 | 0.031 |
| 6 | 90% Mulch/10% BAC | 45% | 0.5% | 0.32 | 0.050 |
| 7 | 90% Mulch/10% BAC | 45% | 1.0% | 0.78 | 0.051 |
| 8 | 90% Mulch/10% BAC | 45% | 1.5% | 1.43 | 0.053 |
| 9 | 90% Mulch/10% BAC | 45% | 2.0% | 1.13 | 0.071 |
| 10 | 80% Mulch/20% BAC | 45% | 0.5% | 0.45 | 0.040 |
| 11 | 80% Mulch/20% BAC | 45% | 1.0% | 0.60 | 0.037 |
| 12 | 80% Mulch/20% BAC | 45% | 1.5% | 0.98 | 0.054 |
| 13 | 80% Mulch/20% BAC | 45% | 2.0% | 1.90 | 0.075 |
| 14 | 70% Clay/30% BAC | 10% | 0.5% | 0.37 | 0.042 |
| 15 | 70% Clay/30% BAC | 10% | 1.0% | 0.44 | 0.031 |
| 16 | 70% Clay/30% BAC | 10% | 1.5% | 0.65 | 0.055 |
| 17 | 70% Clay/30% BAC | 10% | 2.0% | 1.15 | 0.074 |

EXAMPLE III

Hydraulic Mulch Containing Bacterial Cellulose Binding Agent and Fertilizer

Prior to application of hydraulic mulches, the mulch material is generally mixed with a type of grass seed, a tackifier and a fertilizer. Grass seed and fertilizers useful in this embodiment of the present invention are known and commercially available. To demonstrate the effect of the presence of a fertilizer on the tackified hydraulic mulch, BAC was admixed with urea to form a tackifier/fertilizer combination. An exemplary tackifier/fertilizer combination was made by mixing powdered urea tion. To test this alternative embodiment, fresh red alder chips were refined using a Sunds Defibrator CD-300 pilot plant refiner to simulate the commercial refining process used to produce Silva-Fiber®. This mulch is referred to as "Refiner" mulch. Refiner mulch had very similar physical properties to the Silva-Fiber® commercial mulch.

In test samples were BAC tackifier was added to the Refiner Mulch during refining, BAC was metered into the chip screw-feed section of the refiner. The refiner was run for 10 minutes with BAC to equilibrate the process, and mulch samples taken every 5 minutes thereafter were analyzed in accordance with conventional techniques. Based upon the throughput of the refiner, BAC was introduced into the refiner to achieve levels of 1.5% and 3.0% BAC (w/w BAC/total tackified mulch slurry on dry basis). BAC was also introduced to Refiner Mulch after refinement as described previously with reference to Silva-Fiber ®.

Production and evaluation of test pads was conducted in accordance with the procedures set forth above. In addition to the Refiner Mulch test pads, test pads were made using commercial Silva-Fiber ® mulch with no BAC added, and with BAC added after the mulch was formed, as described in Example I. Test pads made from Refiner mulch having no BAC added, and with BAC added during and after refining were also tested. The results are shown below in Table IV.

TABLE IV

| Mulch Source | BAC Added (% Dry Wt.) During Refining | After Refining | Basis Wt. g/m² | Tensile Index Dry Nm/g | Wet Nm/g |
|---|---|---|---|---|---|
| Silva-Fiber ® | 0 | 0 | 676 | 0.21 | 0.05 |
| Silva-Fiber ® | 0 | 1.5 | 733 | 1.82 | 0.20 |
| Refiner | 0 | 0 | 787 | 0.22 | 0.04 |
| Refiner | 0 | 1.5 | 806 | 1.46 | 0.16 |
| Refiner | 0 | 3.0 | 907 | 0.80 | 0.17 |
| Refiner | 1.5 | 0 | 664 | 0.60 | 0.17 |
| Refiner | 3.0 | 0 | 734 | 1.95 | 0.19 |

The experimental results demonstrate that addition of BAC tackifier to both Silva-Fiber ® and Refiner mulch results in an increase in the wet and dry tensile strengths compared to the control samples, whether BAC is introduced during or after mulch refining. Addition of BAC tackifier during mulch refinement may provide handling advantages, since additional mixing and blending equipment would not be required to prepare the hydraulic mulch for application.

EXAMPLE V

Drying the Refined Mulch Containing Tackifier

Generally, methods for producing a tackified hydraulic mulch include drying the tackified mulch after refining is completed. The materials produced in Example IV, with the exception of the Silva-Fiber ® mulch controls, were tested at different moisture contents to determine the effect of tackified mulch moisture content on tensile strength. Each of the test materials was divided into two samples. One was air dried for several days prior to the production of test pads and testing thereof. The other sample was tested without drying. Moisture content was determined on a total weight basis, and tensile indices were determined as described above. The results of this experiment are shown in Table V.

TABLE V

| Drying | BAC Added (% Dry Wt.) During Refining | After Refining | Moisture Content (total weight basis) | Tensile Index Dry Nm/g | Wet Nm/g |
|---|---|---|---|---|---|
| Air | 0 | 0 | 9.2 | 0.18 | 0.02 |
| Air | 0 | 1.5 | 9.2 | 1.46 | 0.12 |
| None | 0 | 1.5 | 62.8 | 1.46 | 0.16 |
| Air | 1.5 | 0 | 8.8 | 0.51 | 0.06 |
| None | 1.5 | 0 | 57.0 | 0.60 | 0.07 |
| Air | 0 | 3.0 | 11.2 | 0.75 | 0.20 |
| None | 0 | 3.0 | 61.9 | 0.80 | 0.17 |
| Air | 3.0 | 0 | 8.6 | 0.71 | 0.08 |

TABLE V-continued

| Drying | BAC Added (% Dry Wt.) During Refining | After Refining | Moisture Content (total weight basis) | Tensile Index Dry Nm/g | Wet Nm/g |
|---|---|---|---|---|---|
| None | 3.0 | 0 | 57.6 | 1.95 | 0.19 |

Differences in tensile indices of dried and undried samples were not significant. This demonstrates that tackified mulch can be dried without losing important properties. Drying of the tackified mulch may provide materials handling advantages.

EXAMPLE VI

BAC Binding Agents for Fibrous Products

In another embodiment of the present invention, BAC is used as a binding agent for fibrous products. Experiments were conducted to demonstrate the efficacy of BAC in binding fibrous products comprising wood pulp fibers treated with bulking agents known as high bulk fluff and hereafter referred to as "treated wood pulp".

Several sets of test pads comprising treated wood pulp and various concentrations of BAC binding agent were formed in accordance with the test procedures set forth above. A separate set of control test pads (i.e., pads having no added BAC binding agent) was also tested. Tensile indices were measured as described above. Test results are summarized in Table VI.

TABLE VI

| BAC DRY WT. (%) | AVE. PAD BASIS WT. (g/m²) | TENSILE INDEX DRY (Nm/g) | WET (Nm/g) |
|---|---|---|---|
| % | 108 | 0.02 | 0.02 |
| 1% BAC | 122 | no test | 0.02 |
| 2.5% BAC | 120 | 1.1 | 0.04 |
| 5% BAC | 128 | 4.4 | 0.11 |
| 10% BAC | 122 | 5.0 | 0.18 |

As shown in Table VI, both wet and dry tensile indices of the treated wood pulp product increased as the concentrations of BAC binding agent increased when concentrations of BAC exceeded 1.0% (total dry weight).

As noted earlier, the natural hydrophilicity of the BAC binding agent greatly enhances the absorbency of fibrous products with which it is used. In this regard, a straightforward test, designated the "wipe/dry" test, was used to confirm the anticipated enhanced absorbency characteristics of the treated wood pulp product incorporating BAC binding agent. The wipe/dry test involves pouring a measured amount of water on a mirror and then wiping the mirror with fibrous product having a predetermined mass or surface area. Each treated wood pulp production including BAC in the amounts specified above removed all of the water on the mirror; no residual water droplets were detected. The absorbency of the treated wood pulp product, as evidenced in the wipe/dry test, is attributable, at least in part, to the natural hydrophilicity of the BAC binding agent. Test pads comprising treated wood pulp having characteristics similar to the control test pads (0% BAC) typically left residual water droplets in wipe/dry tests similar to those described previously.

EXAMPLE VII

BAC Binding Agents for Non-Wood Fibers

To demonstrate the ability of BAC to bind non-wood fibers, rayon fibers (obtained from Mini Fibers, Inc. of Johnson City, Tenn., product code 8E15135) and Kevlar ® fibers (obtained from E. I. DuPont De Nemours & Co. of Wilmington, Del., classified as "short length") were obtained for testing purposes. The rayon fibers were approximately 3 mm in length and of 1.5 denier, while the Kevlar ® fibers were approximately 2 mm in length.

BAC was dispersed in each of the non-wood fiber samples in a standard laboratory British disintegrator with 2 liters of water for 15 minutes (1800 counts). BAC was added at amounts of 0%, 1%, 2.5%, 5% and 10% (w/w, weight of BAC/total fiber weight, dry basis). The resultant fiber slurry was sheeted in a TAPPI (Technical Association of the Pulp and Paper Industry) sheet mold. Each sheet was drained, autocouched with three blotter layers, then dried in a platen drier at 105° C. The resultant sheets, having an average basis weight of about 100 g/m², were cut into two 5×10 cm strips. The tensile index of each strip was determined using a horizontal sample jig attached to a constant strain rate machine (Instron 1122). Wet tensile strengths were determined by spraying water on the samples in the jig until the samples appeared saturated, prior to exerting tension on the strips. The tensile indices of the pads were measured and quantified as described above in Example I. Results of the rayon/BAC sheet experimentation are shown in Table VII, and results of the Kevlar ®/BAC sheet experimentation are shown in Table VIII.

TABLE VII

| BAC Content (dry basis) | Basis Wt. g/m² | Tensile Index Dry, Nm/g | Tensile Index Wet, Nm/g |
| --- | --- | --- | --- |
| 0% | 100 | 0.032 | 0.100 |
| 1% | 101 | 3.74 | 0.388 |
| 2.5% | 102 | 12.7 | 0.601 |
| 5% | 105 | 23.3 | 0.931 |
| 10% | 101 | 37.0 | 1.77 |

Significant improvement in dry tensile strength was observed at 1% BAC levels, and the dry tensile strength continued to improve as larger amounts of BAC were used. Significant improvement in wet tensile strength occurred at 2.5% or 5% BAC levels, and wet tensile strength also significantly improved as larger amounts of BAC were used.

TABLE VIII

| BAC Content (dry basis) | Basis Wt. g/m² | Tensile Index Dry, Nm/g | Tensile Index Wet, Nm/g |
| --- | --- | --- | --- |
| 0% | 109 | 3.21 | 0.501 |
| 1% | 108 | 7.28 | 0.493 |
| 2.5% | 108 | 9.07 | 0.563 |
| 5% | 107 | 13.6 | 0.804 |
| 10% | 107 | 19.0 | 0.934 |

Significant increases in dry tensile index was observed for the Kevlar ®/BAC sheets as the BAC content increased. Some improvement in the wet tensile index was observed at higher BAC levels.

With the information contained herein, various departures from the precise description of the invention will be readily apparent to those skilled in the art to which the invention pertains, without departing from the spirit and the scope of the invention claimed below. The present invention is not to be considered limited in scope to the procedures, properties or components defined, since the preferred embodiments and other descriptions are intended only to be illustrative of particular aspects of the invention. Any procedure, property or method of producing similar products which are functionally equivalent to those described are considered to be within the scope of the invention.

We claim:

1. A method for binding biomass fragments selected from the group consisting of: natural wood fragments; chemically or physically treated wood fragments; natural or treated plant-derived fragments; and combinations thereof having average fragment lengths of at least about 0.3 inches and average fragment diameters of at least about 0.02 inches, which comprises mixing the biomass fragments with a binder comprising microbially produced cellulose formed under agitated culture conditions by Acetobacter microorganisms to distribute the microbially produced cellulose over the surface of the biomass fragments and adhere the microbially produced cellulose to the biomass fragments.

2. The method of claim 1, wherein said microbially produced cellulose is mixed with biomass during refining of said biomass to form said biomass fragments.

3. The method of claim 1, further comprising the step of mixing said biomass fragments with an aqueous solution to produce a slurry prior to mixing said biomass fragments with said microbially produced cellulose.

4. The method of claim 1, further comprising the step of mixing said microbially produced cellulose with water to produce a slurry.

5. The method of claim 1, wherein said microbially produced cellulose is mixed with an inert extender material capable of reducing the moisture content of the binder.

6. A method according to claim 1, wherein said microbially produced cellulose is mixed with said biomass fragments to provide a mixture comprising from about 0.2% to 20% microbially produced cellulose.

7. A method according to claim 6, wherein aqueous liquid is mixed with said mixture to achieve a solids content of about 1% to about 50%.

8. A method according to claim 1 wherein the wet tensile strength of discrete pads formed with said biomass fragments is increased by at least 100% upon binding of said biomass fragments with said microbially produced cellulose.

9. A composition comprising biomass fragments selected from the group consisting of: natural wood fragments; chemically or physically treated wood fragments; natural or treated plant-derived fragments; and combinations thereof having an average fragment length of at least about 0.3 inches and an average fragment diameter of at least about 0.02 inches and a binding agent comprising microbially produced cellulose formed under agitated cell culture conditions by Acetobacter microorganisms, the microbially produced cellulose being distributed over the surface of and adhered to the biomass fragments.

10. A composition according to claim 9, further comprising aqueous liquid in an amount sufficient to permit the composition to be pumped as a slurry.

11. A composition according to claim 9, wherein said microbially produced cellulose is characterized by a substantially continuous reticulated network of fiber strands, and said cellulosic fiber strands have average fibril diameters of about 0.10 to about 0.20 microns.

12. A composition according to claim 11, wherein said composition is hydrophilic.

13. A composition according to claim 9, additionally comprising an inert extender material.

14. A hydraulic mulch composition comprising a pumpable mixture of biomass fragments having an average particle length of at least about 0.3 inches, and an average particle diameter of at least about 0.02 inches, microbially produced cellulose, and an aqueous liquid whereby the biomass fragments bind to one another as a consequence of distribution of the microbially produced cellulose over the surface of the biomass fragments and adherence of the microbially produced cellulose to the biomass fragments.

15. A hydraulic mulch according to claim 14, comprising from about 0.2% to about 20% microbially produced cellulose.

16. A hydraulic mulch according to claim 14, having a solids content of about 1% to about 50%.

* * * * *